United States Patent [19]
Lindskog et al.

[11] Patent Number: 5,861,167
[45] Date of Patent: Jan. 19, 1999

[54] SURFACE ETCHING

[75] Inventors: Sven Lindskog, Stockholm; Leif Blomlöf, Lidingö, both of Sweden

[73] Assignee: Biora AB, Malmo, Sweden

[21] Appl. No.: 809,237

[22] PCT Filed: Sep. 14, 1995

[86] PCT No.: PCT/SE95/01041

§ 371 Date: May 12, 1997

§ 102(e) Date: May 12, 1997

[87] PCT Pub. No.: WO96/09029

PCT Pub. Date: Mar. 28, 1996

[30] Foreign Application Priority Data

Sep. 22, 1994 [SE] Sweden ................................... 9403191

[51] Int. Cl.$^6$ ....................................................... A61F 2/02
[52] U.S. Cl. ........................... 424/423; 523/113; 523/115; 523/116
[58] Field of Search ..................................... 424/423, 434; 523/113, 115, 116

[56] References Cited

U.S. PATENT DOCUMENTS 4,850,872 7/1989 Goldman et al. ........................ 433/215

OTHER PUBLICATIONS

Cao, Zhizhong, et al. "A Scanning Electron Microscopic Observation of Inner Carious Dentin after Cleansing and of the Dentin–Resin Interface" *Dental Research*, 1992 23/6, pp. 439–444.

Lasho, David J., et al., "A Scanning Electron Microscope Study of the Effects of Various Agents on Instrumented Periodontally Involved Root Surfaces", *J. Periodontology*, (1993) 54/4 pp. 210–220.

Meryon, S.D., et al. "Smear Removal Agents: a Quantitative Study in Vivo and in Vitro", *The Journal of Prosthetic Dentistry*, (1987) 57/2 pp. 174–179.

*Primary Examiner*—Carlos A. Azpuru
*Attorney, Agent, or Firm*—Klein & Szekeres, LLP

[57] ABSTRACT

A composition for use in biological, mineralized surface conditioning, especially tooth root conditioning, by selective removal of parts of an exposed tooth root surface so as to improve subsequent attachment of the tooth in conjunction with periodontal surgery, includes, as an active constituent, an effective amount of ethylene-diaminotetraacetic acid (EDTA) in combination with an aqueous matrix. A method of tooth root conditioning includes, in a preferred embodiment, the step of applying to an exposed tooth root surface a viscous composition of EDTA in a concentration of no less than 80% by weight of the concentration at saturation of EDTA.

29 Claims, No Drawings

SURFACE ETCHING

The present invention relates to a method for biological, mineralized surface conditioning, especially tooth root conditioning, by selective removal of parts of an exposed root surface, such conditioning being used as an overture to improve attachment of the tooth in connection with periodontal surgery.

The teeth are attached to the alveolar bone through their roots. A thin layer of mineralized cementum is found along the surface of the roots. The cementum layer anchors collagen fibres which extend to the adjacent alveolar bone. The space, thus created between the root and the bone surfaces, is occupied mainly by collagen fibres and connective tissue cells (fibroblasts). The soft tissue, known as the periodontal membrane or ligament, is a highly specialized connective tissue. It has the capacity to form bone as well as cementum and can, provided the right conditions are given, form a new attachment apparatus in areas of the root where it has been lost to periodontal disease.

Periodontal disease is, second to tooth decay, the most frequent oral disease. It is a progressive disease and affects, in its severe form, approximately 10% of the population in the industrialized countries, leading to partial or complete tooth loss. However, most adults have one or more teeth affected by the disease.

The disease is, in its most common form known as marginal periodontitis. It is caused by accumulation of bacterial deposits on tooth surfaces along the gingival margins. These bacterial deposits originate from the hosts indigenous oral microflora and elicit an inflammatory reaction in the gingiva which results in destruction of tooth-supporting tissues (periodontal membrane and alveolar bone). The destruction of tooth-supporting tissues results in a deepening of the space (periodontal pocket) between the root of the tooth and the gum tissue (gingiva). The disease progresses as bacteria migrate apically into the periodontal pocket, which deepens more and more as a result of the soft tissue inflammation. Unless adequate treatment is instigated, the tooth becomes mobile and will eventually fall out when too much of the tooth-supporting tissues have been destroyed.

The overall aim of conventional treatment of marginal periodontitis is to remove bacterial deposits and dental calculus (mineralized bacterial deposits) from the root surfaces in order to eliminate the cause of gingival inflammation. Conventional treatment can be divided into non-surgical and surgical procedures.

Normally, treatment starts by scraping (scaling and root planing) the tooth surfaces in order to remove both visible bacterial deposits and dental calculus and deposits hidden below the gingival margin. This reduces gingival swelling caused by inflammation and often reduces the depth of the periodontal pockets. However, adequate scaling and root planing performed below the gingival margin is difficult and in deeper periodontal pockets inaccessible infected sites will serve as reservoirs for reinfection. This is often the case for teeth with furcation involvements where the infection has spread to the area inbetween the roots. Consequently, surgical procedures, which will enhance access and visibility, may have to be used to completely eliminate soft and hard bacterial deposits.

During periodontal surgery, the periodontitis-affected roots are exposed by detaching the gingiva from the roots and alveolar bone. The roots are then freed from bacterial deposits and dental calculus by scaling and root planing. This involves also removal of granulation tissue and root cementum contaminated by bacterial toxins. After the area has been cleaned, the gingival flaps are repositioned and sutured. Oral hygiene must be maintained at a high level during the subsequent healing period to avoid recurrent disease.

Such conventional treatment procedures are conservative and will only, at best, preserve the remaining tooth-supporting tissues. Thus, tooth support that has already been lost cannot be recreated by conventional treatment.

Periodontal healing is a primary concern in the treatment of periodontal disease. This is a process largely dependent on the tissue reactions taking place at the hard/soft tissue interface on the root surface.

Long-term studies on healing of periodontal wounds with marginal communication following periodontal treatment have indicated that cellular colonization of the wounded area results from a competition between alveolar bone, oral epithelium and mucosal connective tissue as well as periodontal connective tissue. As a rule a long junctional epithelium will cover the exposed connective tissue of the soft tissue flaps following periodontal surgery, i.e. migrate apically to or close to its presurgical level. Proliferating epithelial cells normally reach the presurgical level of the periodontal pockets approximately one week after surgery, thus preventing connective tissue to attach to the root surface. It has also been established that marginal healing following non-surgical treatment procedures, such as root planing, favours apical proliferation of the pocket epithelium. Furthermore, healing of marginal periodontal wounds does not normally involve formation of reparative cementum or alveolar bone. An exception to this is sometimes seen in the most apical 0.1 to 0.2 mm of the root surface of marginal periodontal wounds, which can be colonized by connective tissue cells before the epithelium reaches the apical extension of the wound. "Bone-fill" has been recorded clinically under favorable anatomical conditions, such as deep vertical destructions. However, most often deep furcation involvements do not lend themselves to successful periodontal healing with conventional periodontal surgery.

In conclusion, the tooth-supporting tissues (cementum, periodontal membrane and alveolar bone) will not normally regenerate after conventional treatment of marginal periodontitis. Instead, the exposed root surface will be covered by a layer of epithelial cells which does not provide a functional attachment for the root.

Research during the seventies and eighties has shown that under favorable conditions periodontal ligament and cementum cells may be encouraged to repopulate a previously diseased root surface. By inserting a semiporous membrane ("Guided Tissue Regeneration") under the soft tissue flap during periodontal surgery epithelial cell migration along the root surface can be prevented and colonization of the root surface by periodontal fibroblasts is thus facilitated. This will allow for selective repopulation by cells from the periodontal ligament and alveolar bone on the root surface.

Etching during periodontal surgery is performed with three aims: removal of bacterial toxins, removal of smear layer and exposure of collagenous fibres in the root surface and increase visibility through hemostatic effects. Of these the two first have been evaluated in vitro employing mainly citric acid and to some extent ortho-phosphoric acid both of which operate at a pH of around 1 (Lowenguth R A, Blieden T M. Periodontal regeneration: root surface demineralization. Periodontology 2000 1993; 1:54).

Scaling and root planing is performed to remove bacterial deposits, calculus and the superficial layers of the root surface (cementum and dentin), structures and tissues which harbour bacterial toxins. Such toxins are not only confined to the bacterial deposits but are also found adsorbed to periodontally diseased root surfaces. These substances have been shown to inhibit cell attachment in vitro, a function necessary for healing. Thus, the aim of scaling and root planing is to provide a biologically acceptable surface for marginal healing. However, following root surface instrumentation, areas of contaminated cementum, as well as a smear layer covering the instrumented surfaces may still remain. Additional root surface treatment, such as etching has been reported to remove the smear layer.

Application of etching agents has been reported to remove smear and debris which may result from scaling and root planing. However, it also affects the mineralized root surface, although contradictory results have been reported depending on mode of application of the agent. Burnishing the root surface with a cotton pellet soaked in citric acid appears to expose more intertubular fibrils and widen dentinal tubules to a greater extent compared to simple application of a drop of the acid or by placing an acid-saturated cotton pellet on the root surface without rubbing, although reports have also indicated no difference. In this respect a prolonged exposure time to the etching agent has been shown to result in an increased penetration depth.

Several studies have studied periodontal healing following citric or ortho-phosphoric acid etching of root surfaces exposed during periodontal surgery, while only few studies have evaluated surrounding soft tissue reactions after acid application. A surprisingly small area of the soft tissue around the site of application appears to suffer any damage despite the low pH (around 1). However, more profound effects on periodontal healing have been reported, although the results appear highly variable.

Since its inception citric and ortho-phosphoric acid etching (pH 1) of root surfaces have been reported to result in new attachment or reattachment. It appears that the approach of etching was inspired by the bone-inductive capacity of factors in demineralized dentin previously termed "Bone Morphogenetic Protein". Later these claims have been disputed, and most in vivo studies indicate that connective tissue healing with some reparative cementum formation will result rather than formation of a long epithelial junction. There is also reason to believe that application of citric or ortho-phosphoric acid to a periodontal wound during surgery will increase visibility through hemostatic effects as well as facilitate removal of granulation tissue.

While the prior art concerned with tooth root conditioning, mainly using citric and to some extent ortho-phosphoric acids the present invention aims at an entirely new concept for such conditioning by resorting to a true etching procedure resulting in greatly improved conditioning to improve subsequent attachment of the tooth. Since the present invention is concerned with etching of the tooth root it is important to note that by etching is meant selective removal of part(s) or component(s) from a solid surface through the action of an etching agent, such as an acid solution or other agent. Etching is thus not concerned with erosion of the treated surface to remove a complete surface layer. Etching performed on a root surface in connection with periodontal surgery thus aims at selectively removing bacterial toxins and hydroxyapatite leaving an exposed layer of collagen.

Accordingly, the present invention has for a main object to provide a method for biological, mineralized surface conditioning, especially by tooth root conditioning an etching procedure to leave an exposed layer of collagen on the tooth root.

Another object of the invention is to provide a composition for use in such method.

Yet another object of the invention is to provide tooth root conditioning techniques, whereby subsequent attachment of the tooth in conjunction with periodontal surgery will be greatly improved.

Still another object of the invention is to provide conditioning techniques which are neither dependent on a low pH, nor do present any toxicological problems.

Yet another object of the invention is to provide conditioning techniques, whereby necrotizing effects on surrounding periodontal tissues are eliminated since conditioning can be operated at or around a neutral pH.

For these and other objects that will be clear from the following detailed description the invention provides a method for the conditioning of biological, mineralized surfaces, and the method according to the invention involves etching treatment of said surface with a composition comprising an effective amount of ethylene-diaminotetraacetic acid (EDTA). The invention is particularly applicable to a root conditioning by selective removal of parts of an exposed tooth root surface, whereby subsequent attachment of the tooth will be greatly improved.

According to a preferred embodiment of the invention the composition contains said acid in an aqueous environment in combination with an aqueous matrix.

The invention also provides for a composition for use in tooth root conditioning constituted by etching to selectively remove parts of an exposed tooth root surface. Said composition contains as an active constituent an effective amount of EDTA in combination with an aqueous matrix or carrier.

To facilitate introduction of the aminopolycarboxylic acid into the composition matrix it is preferred to include a pH-controlling agent in an amount resulting in a pH of the aqueous phase of the composition lying within the range from about 6 to about 8. A particularly preferred range is from about 6.5 to about 7.5, i.e. around neutral, pH 7.

Said pH-controlling agent can be any alkaline compound or substance compatible with the intended use of the composition, and the agent may also be constituted by a suitable buffer. Among alkaline compounds there may be mentioned ammonia and hydroxides of alkali metals and alkaline earth metals. Particularly preferred alkaline compounds are sodium hydroxide, potassium hydroxide and calcium hydroxide.

As indicated earlier the composition is of an aqueous nature and may be constituted by an aqueous solution. For ease of application of the composition it is preferred that it is in the form of a viscous aqueous solution, increased viscosity being provided by a viscosity-increasing agent. Such agent may be constituted by a polysaccharide and may be selected from celluloses and derivatives thereof, starches and derivatives thereof, plant gums, capsular microbial polysaccharides and algal polysaccharides.

Among preferred polysaccharides there may be mentioned celluloses and derivatives thereof, e.g. ethyl celluloses, hydroxyethyl celluloses, carboxymethyl celluloses, and salts thereof and starches and starch derivatives, such as hydroxyethyl starch. A particularly preferred viscosity increasing agent is sodium carboxymethyl cellulose.

Among microbial polysaccharides there may be xanthan gum, curdlan, pullolan, dextran, and among algal polysaccharides there may be mentioned agar, carageenans, alginic acid.

The concentration of the polysaccharide used in the composition according to the invention may vary within broad limits but a practical upper limit is about 25% by weight of the polysaccharide based on the weight of the composition. However, much lower percentages may be used and a concentration of the order of up to 10% by weight of the polysaccharide, such as about 1 to about 5% by weight, are practically conceivable.

As an alternative to using a polysaccharide as a viscosity-increasing agent there may be used agents selected from proteins and glycoproteins, such as gelatin, denatured structural proteins and proteoglycans.

It is preferred that the composition contains water as a major component, and its content of the etching ingredient, EDTA, may be a concentration near saturation or at saturation, such as about 27% by weight based on the water contents of the composition. At around neutral pH the saturation point for the acid, EDTA, lies between about 22 and 27% by weight based on the water contents of the composition, such as about 25%.

The expression "near saturation" means in this disclosure a concentration which is no less than about 80% and especially no less than about 90% of the concentration at saturation.

To facilitate application of the composition according to the invention onto the tooth root surface to be conditioned it is preferred that the composition has a relatively high viscosity, and the composition may for this purpose take the form of a gel or semi-fluid material. Such state or form can be obtained by using a suitable polysaccharide in a relatively small amount, such as up to about 5% by weight based on the water contents of the composition, a preferred range being from about 2 to about 5% by weight.

EDTA is an agent which chelates divalent cations, such as $Ca^{2+}$, $Mg^{2+}$, $Fe^{2+}$ and $Pb^{2+}$. It is widely used in infusion solutions for detoxification and as an anticoagulant in vivo. In vitro it has a variety of uses such as to detach cells from solid substrata, decalcification of tissue specimens before sectioning and staining and as a detergent in biochemical analysis.

With conventional etching agents operating at pH 1, not only the mineral component of exposed dentin surfaces is dissolved but also the collagenous matrix. Collagen is dissolved at acid pH by acids such as citric acid already at weak concentrations. Arguably, EDTA can also dissolve parts of the collagen molecule or superstructure. However, this effect is negligible during the short exposure intended for root surface etching. Thus, EDTA etching in contrast to conventional etching agents will selectively remove hydroxyapatite but not the collagenous matrix of dentin.

As a preferred embodiment the invention resides in an aqueous composition for use in tooth root conditioning by selective removal of an exposed tooth root surface so as to improve subsequent attachment of the tooth in conjunction with periodontal surgery, said composition comprising, based on the water contents of said composition:

EDTA in an amount of about 22 to 27% by weight;

sodium hydroxide as a pH-controlling agent in an amount resulting in a pH within the range about 6.5 to about 7.5; and a viscosity-increasing agent constituted by carboxymethyl cellulose (CMC) or a salt thereof in an amount of from about 1% by weight to about 5% by weight.

A particularly preferred composition for such use is one wherein:

the amount of EDTA is about 25% by weight;

the pH of the composition is around neutral, pH 7; and the viscosity-increasing agent is sodium carboxymethyl cellulose in an amount of about 3 to 5% by weight.

The present invention will be further illustrated below with reference to specific examples which, however, must not be construed to limit the scope of the invention otherwise than as defined in the appended claims. In these examples percentages refer to weight unless otherwise stated.

EXAMPLE 1

Scanning Electron Microscopic (SEM) Investigations

Extracted teeth with exposed dentin were immersed into aqueous solutions of citric acid (saturaded, pH 1), ortho-phosphoric acid (37%, pH 1) or EDTA (24%, pH 7, NaOH) for different periods up to 10 minutes. The specimens were then prepared for SEM examination.

All the solutions removed smear and debris within a short period of time (less than 1 minute). Conventional acid etching (citric or ortho-phosphoric acid) produced an essentially smooth dentin surface with only occasional amorphous deposits in the area between the dentinal tubules, but no fibres visible. Dentinal tubules were clearly visible and appeared widened. EDTA etching produced a completely different texture with the dentin inbetween dentinal tubules consistently displaying a fibrous meshwork, with individual fibres clearly visible and comparable in size to collagenous fibres.

It is interesting to note the almost total lack of fibres after ortho-phosphoric acid application in contrast to the result following EDTA application. EDTA application has exposed fibres in the surface while this was not the case for any of the two acids operating at a low pH.

EXAMPLE 2

Collagen Staining Investigations

Extracted teeth with exposed dentin were immersed into aqueous solutions of citric acid (saturated, pH 1), ortho-phosphoric acid (37%, pH 1) or EDTA (24%, pH 7) for different periods up to 10 minutes. The specimens were then stained with a collagen stain and the staining intensity was assessed densitometrically.

Staining for collagen was significantly more intense for all surfaces treated with EDTA compared to those treated with conventional acid etching (citric or ortho-phoshoric acid). Conventional etching failed almost completely to reveal collagen in the dentin surface.

It is important to note the intense staining for collagen following EDTA application in contrast to the negligible staining following application of any of the two other acids.

The results from these two studies show that the collagenous matrix is left intact following EDTA etching while etching with conventional etching agents such as citric or ortho-phosphoric acids will dissolve both the mineral and the collagenous matrix.

What is claimed is:

1. A method for the conditioning of an exposed biological mineralized surface by selective removal of parts of the exposed surface comprising applying of a viscous composition comprising ethylene-diaminotetraacetic acid (EDTA) in a concentration of no less than 80% by weight of the concentration at saturation of EDTA on said surface.

2. A method according to claim 1, wherein the composition comprises EDTA in a concentration of no less than 90% by weight of the concentration at saturation of EDTA.

3. A method according to claim 1, wherein the composition comprises EDTA in combination with an aqueous matrix.

4. A method according to claim 3, wherein the concentration of EDTA is in a range of from about 22% to about 27% by weight.

5. A method according to claim 3, wherein the concentration of EDTA is about 25% by weight.

6. A method according to claim 3, wherein the concentration of EDTA is about 24% by weight.

7. A method according to claim 1, wherein the biological mineralized surface is an exposed tooth root dentin surface, and wherein the selective removal step comprises the selective removal of parts of the exposed tooth root dentin surface so as to improve subsequent attachment of the tooth in conjunction with periodontal surgery.

8. A composition comprising a viscous solution of EDTA in a concentration of no less than 80% by weight of the concentration at saturation of EDTA.

9. A composition according to claim 8 wherein the solution comprises EDTA in a concentration of no less than 90% by weight of the concentration at saturation of EDTA.

10. A composition according to claim 8 wherein the solution comprising EDTA in combination with an aqueous matrix.

11. A composition according to claim 10, wherein the concentration of EDTA is in a range of from about 22% to about 27% by weight.

12. A composition according to claim 10, wherein the concentration of EDTA is about 25% by weight.

13. A composition according to claim 10, wherein the concentration of EDTA is about 24% by weight.

14. A composition according to claim 8, characterized by further comprising a pH-controlling agent in an amount resulting in a pH of the composition lying within the range from about 6 to about 8.

15. A composition according to claim 14, characterized in that said pH lies within the range from about 6.5 to about 7.5.

16. A composition according to claim 14, characterized in that said pH-controlling agent is selected from the group consisting of alkaline compounds and buffers.

17. A composition according to claim 16, characterized in that said agent is an alkaline compound selected from the group consisting of ammonia and hydroxides of alkali metals and alkaline earth metals.

18. A composition according to claim 8, which is in the form of a viscous aqueous solution.

19. A composition according to claim 18, characterized by comprising a viscosity-increasing agent selected from the group consisting of polysaccharides, proteins, and glycoproteins.

20. A composition according to claim 19, characterized in that said agent is selected from the group consisting of celluloses and derivatives thereof, starches and derivatives thereof, plant gums, capsular microbial polysaccharides, and algal polysaccharides.

21. A composition according to claim 19, characterized in that said agent is selected from the group consisting of carboxymethylcellulose and a salt thereof.

22. An aqueous composition for use in tooth root conditioning by selective removal of an exposed tooth root surface so as to improve subsequent attachment of the tooth in conjunction with periodontal surgery, comprising, based on the water contents of said composition:

EDTA in an amount of about 22% to about 27% by weight;

sodium hydroxide as a pH-controlling agent in an amount resulting in a pH within the range about 6.5 to about 7.5; and a viscosity-increasing agent selected from the group consisting of carboxymethyl cellulose (CMC) and a salt thereof in an amount of from about 1% by weight to about 5% by weight.

23. A composition according to claim 22, wherein:

the amount of EDTA is about 25% by weight;

the pH of the composition is around neutral, pH 7; and the viscosity-increasing agent is sodium carboxymethyl cellulose in an amount of about 3% to about 5% by weight.

24. A method for the conditioning of an exposed biological mineralized surface by selective removal of parts of the exposed surface, comprising treating said surface with a viscous composition comprising an effective amount of ethylene-diaminotetraacetic acid (EDTA).

25. A method according to claim 24, characterized in that said surface is associated with a tooth root whereby improved subsequent attachment of the tooth in conjunction with periodontal surgery is obtained.

26. A method according to claim 24, characterized in that said effective amount equals a concentration near or at saturation of said acid in an aqueous matrix.

27. A compositon according to claim 11, wherein the concentration of EDTA is in a range of from about 22% to about 24% by weight.

28. A composition according to claim 21, wherein the concentration of carboxymethylcellulose or a salt thereof is about 1% to about 3% by weight.

29. A composition according to claim 22, wherein the amount of EDTA is about 22% to about 24% by weight; and wherein the viscosity increasing agent is sodium carboxymethylcellulose in an amount of about 1% to about 3% by weight.

* * * * *